US008828234B2

(12) United States Patent
Bisschops et al.

(10) Patent No.: US 8,828,234 B2
(45) Date of Patent: *Sep. 9, 2014

(54) DEVICE FOR CHROMATOGRAPHIC SEPARATIONS

(75) Inventors: Marc Abtonius Theodorus Bisschops, Breda (NL); Jozef Anton Mari Pennings, The Hague (NL); Jacob Arthur Tijsterman, Haarlem (NL)

(73) Assignee: Xendo Holding B.V., Leiden (NL)

( * ) Notice: Subject to any disclaimer, the term of this patent is extended or adjusted under 35 U.S.C. 154(b) by 945 days.

This patent is subject to a terminal disclaimer.

(21) Appl. No.: 12/962,488

(22) Filed: Dec. 7, 2010

(65) Prior Publication Data

US 2011/0108485 A1    May 12, 2011

Related U.S. Application Data

(62) Division of application No. 12/090,086, filed as application No. PCT/NL2006/000519 on Oct. 13, 2006, now Pat. No. 7,846,335.

(60) Provisional application No. 60/726,415, filed on Oct. 13, 2005.

(30) Foreign Application Priority Data

Oct. 13, 2005 (EP) .................................. 05077342

(51) Int. Cl.
*B01D 15/14* (2006.01)
*B01D 15/18* (2006.01)
*G01N 30/46* (2006.01)
*G01N 30/60* (2006.01)

(52) U.S. Cl.
CPC .......... *G01N 30/468* (2013.01); *B01D 15/1864* (2013.01); *B01D 15/1842* (2013.01); *B01D 15/1885* (2013.01); *B01D 15/14* (2013.01); *G01N 30/6034* (2013.01); *G01N 30/467* (2013.01)
USPC ...................................... 210/656; 210/198.2

(58) Field of Classification Search
CPC ............... B01D 15/14; B01D 15/1821; B01D 15/1864; B01D 15/1885; G01N 30/6034; G01N 30/461; G01N 30/466; G01N 30/467; G01N 30/468
USPC ........................ 210/635, 656, 659, 198.2, 417
See application file for complete search history.

(56) References Cited

U.S. PATENT DOCUMENTS 3,201,922 A    8/1965    Villalobos
3,922,223 A   11/1975    Burkhartsmeier (Continued)

FOREIGN PATENT DOCUMENTS

EP    0 003 617    8/1979
EP    0 818 226    1/1998

(Continued)

OTHER PUBLICATIONS

International Search Report for PCT/NL2006/000519, mailed on Jan. 17, 2007, 2 pages.

(Continued)

*Primary Examiner* — Ernest G Therkorn
(74) *Attorney, Agent, or Firm* — Morrison & Foerster LLP

(57) ABSTRACT

A device is provided for chromatographic separations comprising a manifold comprising a plurality of connectors for connecting to one or more chromatographic separation columns and/or feed or extraction tubing. At least one central duct is formed between at least two connectors forming an inlet and an outlet respectively. The central duct comprises a closable duct valve; and a plurality of branch ducts branching from the central duct to a branch connector. The branch duct comprises a closable branch valve, wherein at least one branch duct is positioned between the inlet and the central duct valve and wherein at least one branch duct is positioned between the outlet and the central duct valve. The device is arranged for carrying out single-column and (continuous) multicolumn chromatographic separations. This allows the purification of biopharmaceutical products without having to develop, demonstrate and validate cleaning procedures for the valves.

5 Claims, 13 Drawing Sheets

(56) References Cited

U.S. PATENT DOCUMENTS

| | | |
|---|---|---|
| 4,581,624 A | 4/1986 | O'connor |
| 4,848,722 A | 7/1989 | Webster |
| 4,883,504 A | 11/1989 | Gerstel et al. |
| 5,176,359 A | 1/1993 | Leveson et al. |
| 5,203,368 A | 4/1993 | Barstow et al. |
| 5,465,748 A | 11/1995 | Bowers |
| 5,470,464 A | 11/1995 | Priegnitz |
| 5,882,523 A | 3/1999 | Hotier et al. |
| 6,017,448 A | 1/2000 | Hotier et al. |
| 6,063,284 A | 5/2000 | Grill |
| 6,149,874 A | 11/2000 | Hotier |
| 6,331,250 B1 | 12/2001 | Kaneko et al. |
| 6,402,959 B1 | 6/2002 | Dessapt et al. |
| 6,409,922 B1 | 6/2002 | Kaneko et al. |
| 6,427,526 B1 | 8/2002 | Davison et al. |
| 6,537,451 B1 | 3/2003 | Hotier |
| 6,544,413 B1 | 4/2003 | Nagamatsu et al. |
| 6,712,963 B2 | 3/2004 | Schick |
| 6,797,175 B2 | 9/2004 | Hotier |
| 7,052,603 B2 | 5/2006 | Schick |
| 7,544,293 B2 | 6/2009 | Oroskar et al. |
| 7,846,335 B2 * | 12/2010 | Bisschops et al. ............ 210/656 |
| 2002/0088754 A1 | 7/2002 | Tanimura et al. |
| 2003/0230521 A1 | 12/2003 | Schick |
| 2006/0118472 A1 | 6/2006 | Schick et al. |
| 2008/0237132 A1 | 10/2008 | Hotier et al. |
| 2009/0218286 A1 | 9/2009 | Bisschops et al. |
| 2010/0144028 A1 | 6/2010 | Bisschops et al. |

FOREIGN PATENT DOCUMENTS

| | | |
|---|---|---|
| EP | 1 003 036 | 5/2000 |
| EP | 1 178 308 | 2/2002 |
| EP | 1 336 610 | 8/2003 |
| EP | 1 873 520 | 1/2008 |
| JP | 3-134562 | 6/1991 |

OTHER PUBLICATIONS

Chin and Wang, Separation and Purification Reviews (2004) 33(2):77-155.

PTO Translation No. 10-4137 of European Patent No. 3617.

* cited by examiner

DEVICE FOR CHROMATOGRAPHIC SEPARATIONS

CROSS-REFERENCE TO RELATED APPLICATIONS

This application is a divisional of U.S. application Ser. No. 12/090,086 having an international filing date of 13 Oct. 2006, now U.S. Pat. No. 7,846,335, issued 7 Dec. 2010, which is the national phase of International Application No. PCT/NL2006/000519 having an international filing date of 13 Oct. 2006, which claims priority from European Application No. 05077342.3, filed 13 Oct. 2005, and which claims priority under 35 U.S.C. §119(e) to U.S. Provisional Application No. 60/726,415, filed 13 Oct. 2005, which is hereby incorporated by reference as if fully set forth. The contents of these documents are incorporated herein by reference.

FIELD OF THE INVENTION

The invention relates to a device for chromatographic separations. In particular, the invention relates to a modular chromatography system for single or multiple columns that is suitable for purification of biopharmaceutical products.

BACKGROUND OF THE INVENTION

Chromatography is one of the most important working horses in the purification of biotechnological products. This can be based on ion exchange chromatography, affinity chromatography, size exclusion (or gel filtration) chromatography, hydrophobic interaction chromatography or reversed phase chromatography among others.

Traditionally, chromatographic purifications are carried out in batch mode. This involves one single column that is subsequently loaded, washed, eluted, etc. For treating large volumes or purifying large amounts of product, either very large columns are needed or repeated injections are required. This yields a relatively inefficient mode of operation with a low specific productivity. Such chromatography processes require large amounts of Adsorbent and large amounts of buffers.

Continuous processes are known to have a higher specific productivity and—if carried out in a countercurrent mode—consume much lower amounts of buffer. Continuous countercurrent chromatography processes are generally based on multiple columns. This includes the traditional merry-go-round system, carrousel type systems and static type SMB systems.

Such SMB (Simulated Moving Bed) systems generally use a series of columns with periodically moving inlet and outlet ports. These techniques have been successfully used in the production of petrochemicals and sugars. However, biopharmaceutical production is still based on batch processes. Nonetheless, also batch processes can involve steps that are essentially carried out in a continuous mode. For instance, centrifugation is often performed as a continuous process. In some processes even continuous perfusion systems for the cell culture or fermentation process are being used.

In order to avoid the cleaning of equipment, biopharmaceutical production processes nowadays use wetted components that are for single-use or that are dedicated to one process step of one single product. This cuts down the requirement for cleaning dramatically. In case of single-use wetted components, cleaning can be even completely avoided. The use of single-use bags for storing buffers and intermediate products instead of containers is one very successful example of single-use components in biopharmaceutical industries. In processing relatively small batches, it is also common to use disposable bioreactors, disposable membrane cartridges and tubing.

Existing multicolumn chromatography systems involve complex valve arrangements in order to ensure proper distribution of all flows to all columns. For biotechnology this is undesirable because of the cleaning issues involved. The cleaning of a system in biopharmaceutical production processes should be designed such that it ensures removal of all contaminating compounds from all potentially wetted surfaces. In this respect, equipment with complex internal geometries is very difficult to clean.

Chin and Wang, in "Simulated Moving Bed Equipment Designs", *Separation And Purification Reviews*, Vol 33. No 2, pp 77-155, (2004) give some requirements for a truly versatile SMB system, which includes the possibility of performing zone bypasses and allowing configurations in which the number of zones ranges from three to nine or more, allowing easy changes in the configuration.

In one aspect of the invention, it is desirable to provide a valve device that is flexible in the number of connections that can be made and the number of columns that can be added. In another aspect of the invention it is desirable to provide a valve device that limits contamination by using a specific structure. In case only one column is connected to the system, the system would also be suitable for traditional single-column chromatography processes.

DEFINITIONS

In this document, the following terms shall have the following meanings:

Continuous Multicolumn Chromatography: Continuous Multicolumn Chromatography is a method in which multiple chromatography columns are interconnected to allow continuous operation with respect to the feed solution. This includes among others Simulated Moving Bed chromatography and Merry-Go-Round approaches.

Adsorbent: The Adsorbent is the stationary phase in the chromatography process. Commonly, this comprises particles, but it may also be a structured packing (e.g., a functionalized membrane or a monolithic structure). The Adsorbent normally comprises a matrix (silica, polymeric, polysaccharides, etc.) and may be functionalized (e.g., in case of ion exchange or affinity chromatography).

Column: A column is a single module that contains Adsorbent. In the case of a particulate Adsorbent, the Adsorbent may be in a packed bed or may be fluidized due during the operation.

Zone: One or more columns connected in parallel and/or in series, where each column is essentially subjected to the same flow rate and where no intermediate in- and outlets to and from the zone are present.

Purification: The process in which either the product of interest is isolated from its environment, for instance by binding it to an Adsorbent, or in which contaminants are removed from the environment of the product of interest.

Biopharmaceuticals: Pharmaceutical products that are produced through biotechnological processes. This includes all recombinant proteins, (monoclonal) antibodies, vaccines, blood/plasma-derived products, nonrecombinant culture-derived proteins, and cultured cells and tissues.

Fractionating chromatography: The separation is based on a difference in propagation velocity through the bed. This is commonly caused by differences in affinity for the Adsorbent. In the case of, for instance, size exclusion media, the difference in propagation velocity is caused by the fact that smaller molecules can penetrate the media more easily than larger molecules and are thus retained. Examples of this type of chromatography are size exclusion, ion exclusion, reversed phase chromatography and hydrophobic interaction chromatography.

Elution chromatography: Elution chromatography is the mode of operation where the Adsorbent is subsequently loaded and eluted. Normally, this type of operation involves one or multiple wash steps in the process cycle and in some cases there may even be a regeneration, cleaning and/or equilibration step. The separation is based on the selective adsorption of one or more components from solution, while other components are essentially not retained and move through the column This mode of chromatography includes—for instance—ion exchange and affinity chromatography. The most common affinity chromatography media in the purification of biopharmaceuticals are based on protein A. Nonetheless, a wide variety of other affinity ligands are commercially available or are currently being developed, such as Immobilized Metal Affinity Chromatography (IMAC), heparin, lectin, triazine dyes, etcetera.

Displacement chromatography: A stronger binding component displaces a weaker binding component from the adsorbent. This can for instance occur in chromatographic processes based on hydrophobic interactions or ion exchange. In the context of the present invention, this will be considered a subset of Elution chromatography.

Single-use: Modules, parts, instruments or components are single-use in case they are disposed after a production batch has been terminated or finished. Single-use components are often referred to as disposable components. A well-known example of single-use components are plastic bags to store buffers, solutions or intermediate products instead of rigid containers, such as supplied by Stedim S. A. (Aubagne, France). Other examples are membrane cartridges, such as supplied by Pall (East Hills, N.Y.) or Millipore (Bedford, Mass.).

Dedicated-use: Modules, parts, instruments or components are for dedicated-use in case their application is limited to the purification of one single product. This may involve multiple batches and/or multiple production campaigns.

SUMMARY OF THE INVENTION

In one aspect of the invention a device for chromatographic separations is provided comprising a manifold comprising a plurality of connectors for connecting to one or more chromatographic separation columns and/or feed or extraction tubing. At least one central duct is provided between at least two connectors forming an inlet and an outlet respectively. The central duct comprises a closable duct valve. In addition, a plurality of branch ducts branching from the central duct to a branch connector are provided, the branch duct comprising a closable branch valve. At least one branch duct is positioned between the inlet and the central duct valve and at least one branch duct is positioned between the outlet and the central duct valve.

DETAILED DESCRIPTION OF THE INVENTION

Figure 1:
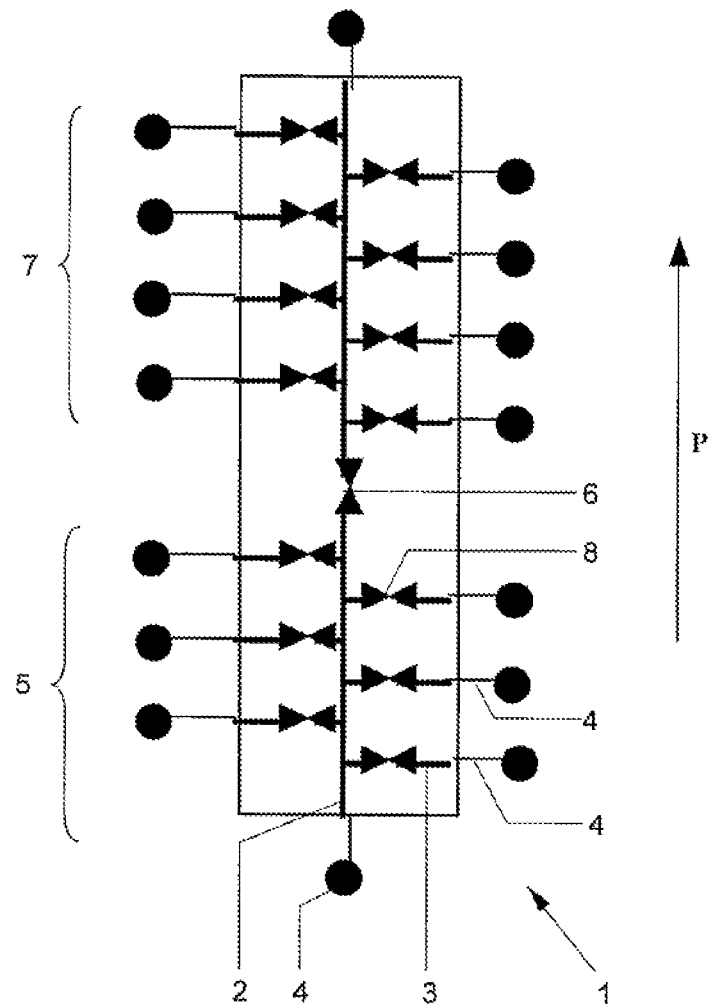
FIG. 1 shows a valve manifold with a direction of flow arrow P.

Traditional chromatography processes are generally carried out using one or sometimes two columns that contain the Adsorbent. For single column systems, the process involves a single pump to direct the different process fluids into the column. Generally, chromatography systems comprise one or more inlet valves at the inlet of the pump and outlet valves at the outlet of the column. These valves allow selection of the appropriate ingoing solutions and collecting waste and product at the outlet of the column separately.

Biopharmaceuticals are generally purified through batch column chromatography processes. Such systems normally involve diaphragm valves. The application of diaphragm valves relies on the fact that these can be easily cleaned. Commercially, such valves are supplied by—for instance— Robolux AB (Lidingo, Sweden), Alfa-Laval (Lund, Sweden) or GEMÜ Gebr. Midler Apparatebau GmbH & Co. KG (Ingelfingen-Criesbach, Germany).

A more efficient method for conducting chromatographic separations is by means of the so-called Merry-go-round process. Such systems essentially comprise generally three columns that can be interconnected. This scheme allows continuous treatment of the feed solution in two columns that are connected in series while the third column is subjected to subsequent washing, eluting and regenerating or equilibrating conditions.

Simulated Moving Bed (SMB) chromatography is a mode of operation that relies on multiple columns that are interconnected. These columns are typically distributed over multiple zones, each of which has its own in- and outlets. The most common SMB process comprises four zones. This allows continuous fractionation of a feed solution into two product solutions, one of which predominantly contains stronger binding component(s) and the other predominantly containing weaker binding component(s). One of the best known large scale SMB processes is the so-called Parex process, which separates para-xylene from a mixture of xylenes. This process is based on the Sorbex SMB technology developed and commercialized by UOP LLC (Des Plaines, Ill.). Other notable examples are the purification of fructose from a mixture of glucose and fructose, the recovery of sucrose from molasses, the recovery of betaine from molasses, the purification of various carboxylic acids and many chiral separations.

Over time, quite some alternative process schemes have been disclosed that are derived from SMB chromatography. This includes the approach described by Japan Organo Co. Ltd. (Tokyo, Japan), the VariCol process from NovaSep, the Sequential SMB from Applexion and the Improved SMB from Nippon Rensui. All systems aim at essentially continuously fractionating a feed solution into two or more product solutions.

SMB technology can also be used for elution chromatography, which involves binding and eluting components under different conditions. The configuration of the columns will then be different than in the traditional four-zone SMB process, since not all zones need to be interconnected. In addition to this, elution chromatography may involve more than four steps, particularly if the elution is followed by a regeneration procedure to remove any irreversibly bound material from the Adsorbent. This is for instance often the case in the recovery of products that are derived from fermentation processes or cell culture processes.

A lot of different systems for continuous chromatography or SMB chromatography have been developed and many different designs are being applied in industry. We will briefly discuss the most relevant systems and their applications. For this brief overview, we will adopt the classification as presented by Chin and Wang.

The first major class of SMB systems relies on a rotating central SMB valve. This includes the Sorbex system developed by UOP. The basic design of the Sorbex valve was disclosed in 1961. Since then, many variations and improvement on this design have been patented. According to Ching and Wang, UOP has installed approximately 130 industrial units worldwide.

Another notable design that relies on a central SMB valve is the ISEP valve and its variations developed by Advanced Separation Technologies (Lakeland, Fla.), now part of Calgon Carbon Corporation, which was developed on the basis of earlier designs. Calgon Carbon Corporation claims over 300 installations worldwide in over 40 different applications. Based on the same concept, Torus B.V. (Haarlem, NL) developed a similar device. Millipore Corporation (Bedford, Mass.) disclosed in U.S. Pat. No. 5,465,748 a similar valve that was claimed to be sanitizable, which would allow SMB applications in the purification of biopharmaceutical industries, but no practical experiences with this device are reported.

A major disadvantage of these systems lies in the fact that the overall system involves a rotating turntable that carries the columns filled with Adsorbent. For this reason, these systems are sometimes referred to as carrousel type SMB systems. In spite of the mechanical issues related to the turntable, systems with more than 100 m3 Adsorbent have been installed. Commercial applications of these systems include recovery of lysine from a fermentation broth, the production of potassium nitrate, sugar deashing, Vitamin C production, purification of bovine immunoglobulins from milk whey and purification of antibiotics.

The disadvantages of carrousel type SMB systems have also led to the development of variations of the central rotary valve in such a way that the columns no longer rotate. Calgon Carbon Corporation (Pittsburgh, Pa.) patented a valve comprising of three parts, of which only the central part rotates and Puritech B.V. (Dessel, Belgium) patented essentially a similar device. These valves, however, lack the flexibility of the carrousel type SMB systems.

The second major class of SMB systems relies on a distributed valve system. These systems rely on a plurality of generic valves, generally two-way, three-way or multiport valves. Two-way valves allow either flow to go through or not. They have one inlet and one outlet and are therefore also known as on-off valves. Multiport valves are available in many configurations. The most common one is the so-called Select Dead-end (SD) configuration with one outlet and multiple inlets. The SD valve connects only the selected inlet to the outlet, while closing all other inlets. The most common SD valve is a rotary valve, such as supplied by Valco Instruments Co. (Houston, Tex.).

The first SMB design based on a distributed valve system was developed by UOP as a lab or pilot scale instrument to support Sorbex technology. This approach has been adopted to implement a variety of configurations or schemes, including the Japan Organo process for multicomponent separations or the Varicol concept commercialized by NovaSep. This concept was also the basis for the systems commercialized by NovaSep S.A.S. for chiral separations. Chin and Wang give a large number of references for these.

Application of two-way valves requires multiple valves per column in order to conduct traditional fractionating chromatography with four zones. For traditional SMB processes, this can be four or six, depending on the configuration chosen. For more complex operations, the number of two-way valves can even be higher. The number of valves can be reduced by applying three-way valves. This is for instance disclosed in systems described by Golem, Green and Moran.

Continuous multicolumn chromatography processes for biopharmaceutical proteins and related products have been investigated on laboratory scale only. This includes mainly work on Size Exclusion Chromatography. Protein A affinity chromatography has been demonstrated in a merry-go-round system, carrousel type SMB and in a static type SMB. The purification of transgenic human serum albumin by means of affinity chromatography has been described for large scale production. None of these processes have been implemented on equipment that is suitable for biopharmaceutical production. The purification of bovine immunoglobulins from milk whey has been disclosed on a carrousel type SMB system.

Aspects of the invention are paraphrased in the following clauses: A modular chromatography system comprising of pumps, columns and valve manifolds, arranged in such a way that it allows purification of a biopharmaceutical from a feed mixture. The valve manifold organizes valves necessary for the chromatography process. The wetted parts of the valve manifold are designed for single-use or for dedicated use; A modular chromatography system comprising of one single pump, one single column and one single manifold, arranged in such a way that it allows single-column chromatographic purification of a biopharmaceutical product from a feed mixture. The central valve will remain closed during operation, while the other valves are operated in such a way that all relevant fluids are applied on the column in the appropriate order. During rinsing and/or cleaning, the central valve may be opened; A system as described previously with two separate manifolds, one serving the inlet and one serving the outlets of the system; An essentially continuous purification process with a system as described previously, in which multiple essentially identical columns carrying a suitable Adsorbent. Such process involves simultaneously conducting at least two of the following steps: loading, washing, eluting, regenerating and equilibrating one or more of the columns; an essentially continuous purification process with a system as described previously, in which multiple essentially identical columns carrying a suitable Adsorbent. Such process may involve continuous fractionation of the feed solution into at least two outlet streams, at least one of each containing essentially purified product; A purification process comprising of multiple chromatographic separations, more than one of which is carried out in a system as described previously. The system comprises different columns, at least one for each individual chromatography step involved, each filled with a suitable Adsorbent for that particular step; a valve manifold with multiple in- and outlets for single-use or dedicated-use, comprising of: a. one inlet that can be connected to the exit of a chromatography column; b. one outlet that can be connected to the inlet of a next chromatography column or to the inlet of the same chromatography column; c. at least two, preferably more inlets through which solutions can be transferred into the column mentioned under (b); d. at least two, preferably more outlets that can be connected to tanks to collect effluents from the column mentioned under (a); e. diaphragm valves that connect the system inlets mentioned under (c) to the inlet of the column mentioned under (b), and the outlets mentioned under (d) to the outlet of the column mentioned under (a); f. actuators that can open or close the diaphragm valves mentioned under (e); in such a way that all parts except from the actuators mentioned under (f) are single-use or for dedicated-use; a valve manifold as described previously in which the diaphragm and conducts are organized in one single piece; a valve manifold as described previously in which the diaphragm and conducts are organized in two separate pieces, one carrying the conducts and a second part being or carrying the diaphragm; a valve manifold as described previously in which the mentioned in- and outlets pass through the manifold in such a way that manifolds can be stacked in series, with only one common in- or outlet for each individual system in- or outlet; a valve manifold as described previously in which the diaphragm and conducts are assembled in one single piece; a valve manifold as described previously in which the diaphragm and conducts are organized in two separate pieces, one carrying the conducts and a second part being or carrying the diaphragm.

According to the invention, the system comprises one or more columns, at least one of which is connected to a valve manifold at the in- and outlets. Furthermore, the system may comprise multiple inlets and outlets. System inlets may be connected to a pump capable of transferring any of the fluids involved into the chromatography process. Alternatively, a system outlet can be connected to the inlet of a subsequent step in the purification process, such as a membrane unit or another chromatography step. For convenience, additional monitors may be connected to the system in- and outlets to monitor relevant process conditions, including (but not limited to) pressure, conductivity, pH or UV absorbance.

Figure 2:
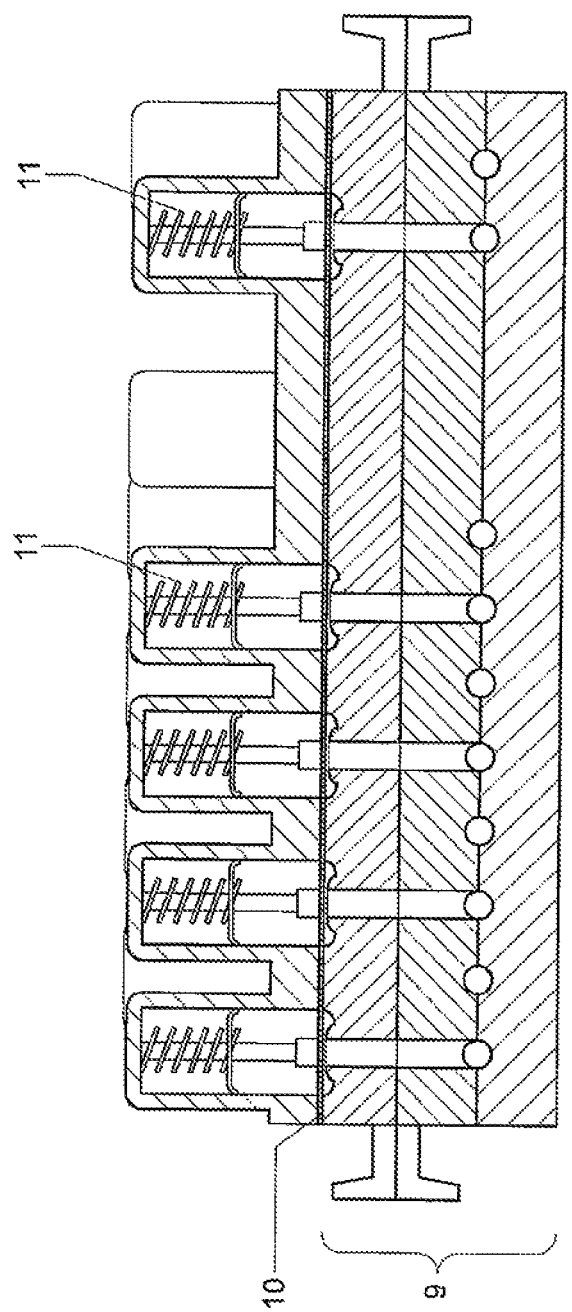
FIGS. 2-6 show typical lay-outs for the valve manifold 1 and parts thereof.

Although the valve device can be construed in a variety of ways, in one aspect, the valve device according to the invention preferably comprise two or three separate construction parts as shown in FIG. 2 and further detailed in FIGS. 3-6.

In such embodiment, a manifold 1 comprises a central duct 2 connectable to an outlet of a column (see for instance the arrangement depicted in FIG. 8) and an inlet of a column. Branch ducts 3 are connectable to system in- and outlets such as feed flows and extraction flows. In addition, depending on the system configuration, the branch ducts 3 may be coupled to column in- and outlets. In general, the central duct 2 provides an efficient flow connection between subsequent columns to be coupled serially and/or parallel by connectors 4, to minimize flow impedances, in particular of the main flow between columns, in the manifold 1. Preferably, system inlets and outlets (not shown) are connected to a branch duct 3 that connects to the central duct 2. In the embodiment shown, the manifold 1 can be coupled to a chromatographic column. In such an arrangement, typically, the flow in a column is from top to bottom in the direction of gravity. Generally, this would imply that the direction of flow in the valve manifold 1 is from bottom to top, that is, according to arrow P in FIG. 1. In such an arrangement, the branch connectors 4 are forming system extraction outlets 5, separated by a central valve 6 in the central duct 2 from branch connectors 4 forming feed inlets 7. In addition, the branch ducts 3 are separated from the central duct 2 by branch duct valves 8. Typically, the connectors can be of any type, and are preferably of a sanitary type such as a connector known in the art as a tri-clover connector. Although the schematic drawing depicts the connectors as protruding elements, alternatively, the connectors can be of a male-female type. Yet as another alternative, the connectors can be of a gasket type, such as will be elaborated further in FIG. 8.

Figure 6:
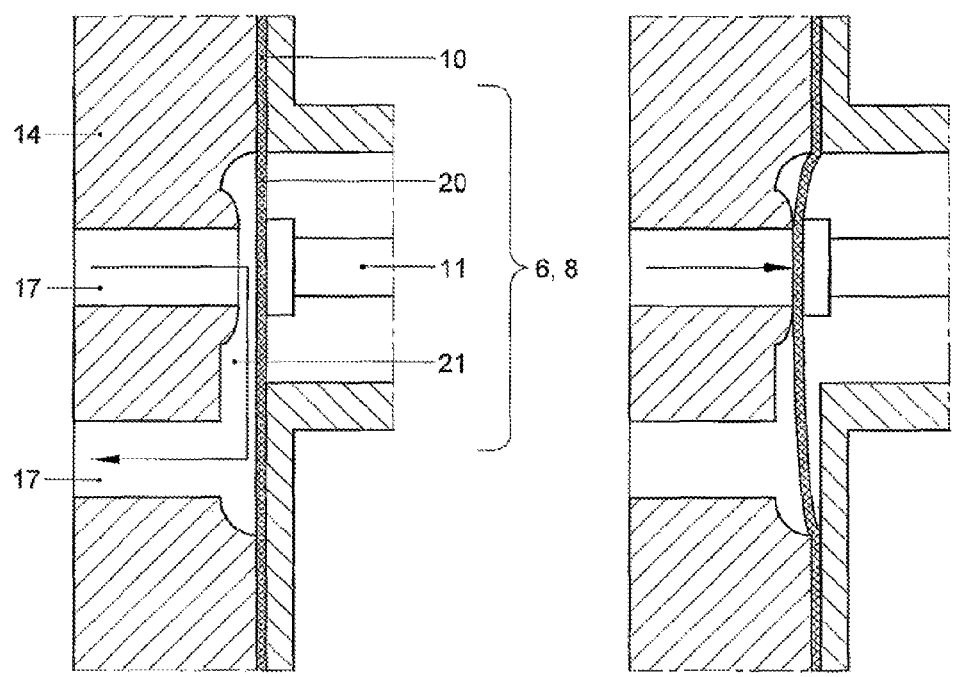

A preferential type of valve, for both central valve and branch duct valves, is a diaphragm valve which is shown as an exemplary embodiment in FIG. 6. This type of valve has a simple geometry and optimally designed wet surfaces which makes it preferable of use in chromatographic processes for biopharmaceutical products, which has a very high requirement on sanitary parts. In this respect, the term "optimally designed" refers to a condition that there is a minimum of dead space and complex geometry which is cumbersome in view of sanitary requirements. However, the invention is not limited to such valves but could incorporate other valves with like sanitary characteristics.

As an example, a typical lay-out for the valve manifold 1 and parts thereof is shown in FIG. 2 to FIG. 6. It may be clear that many alternative configurations and designs can be thought of, which fulfill the same requirements. The drawings included in this document only serve as an illustration. The invention is not limited to the design shown here.

In one aspect of the invention, as shown in FIG. 2, the manifold 1 is formed from a duct layout part 9 and a membrane part 10 for closing the duct layout part 9 and for forming the membrane valves 8, and comprising mountings for mounting a corresponding number of actuators 11.

Figure 3:
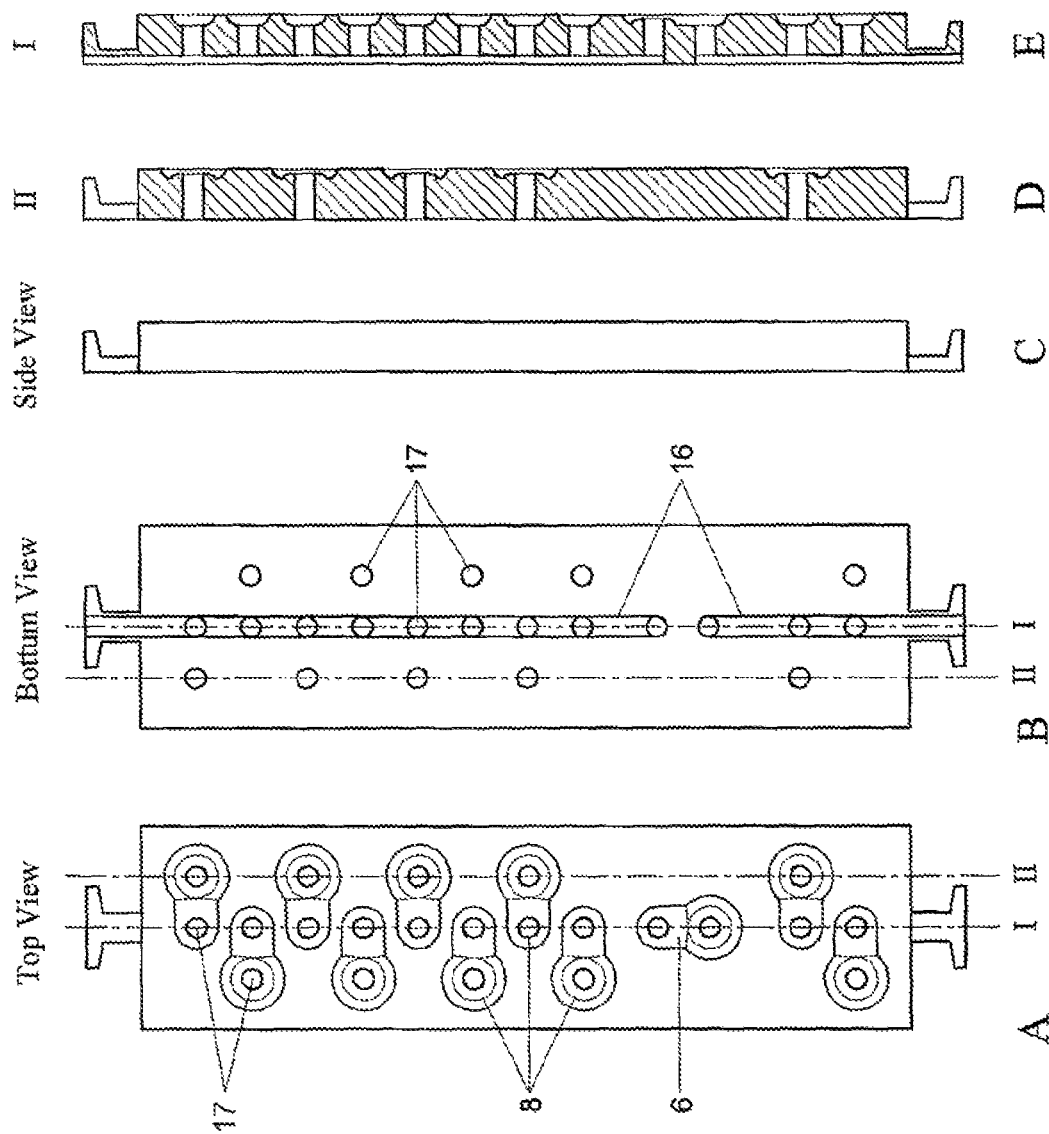
Figure 4:
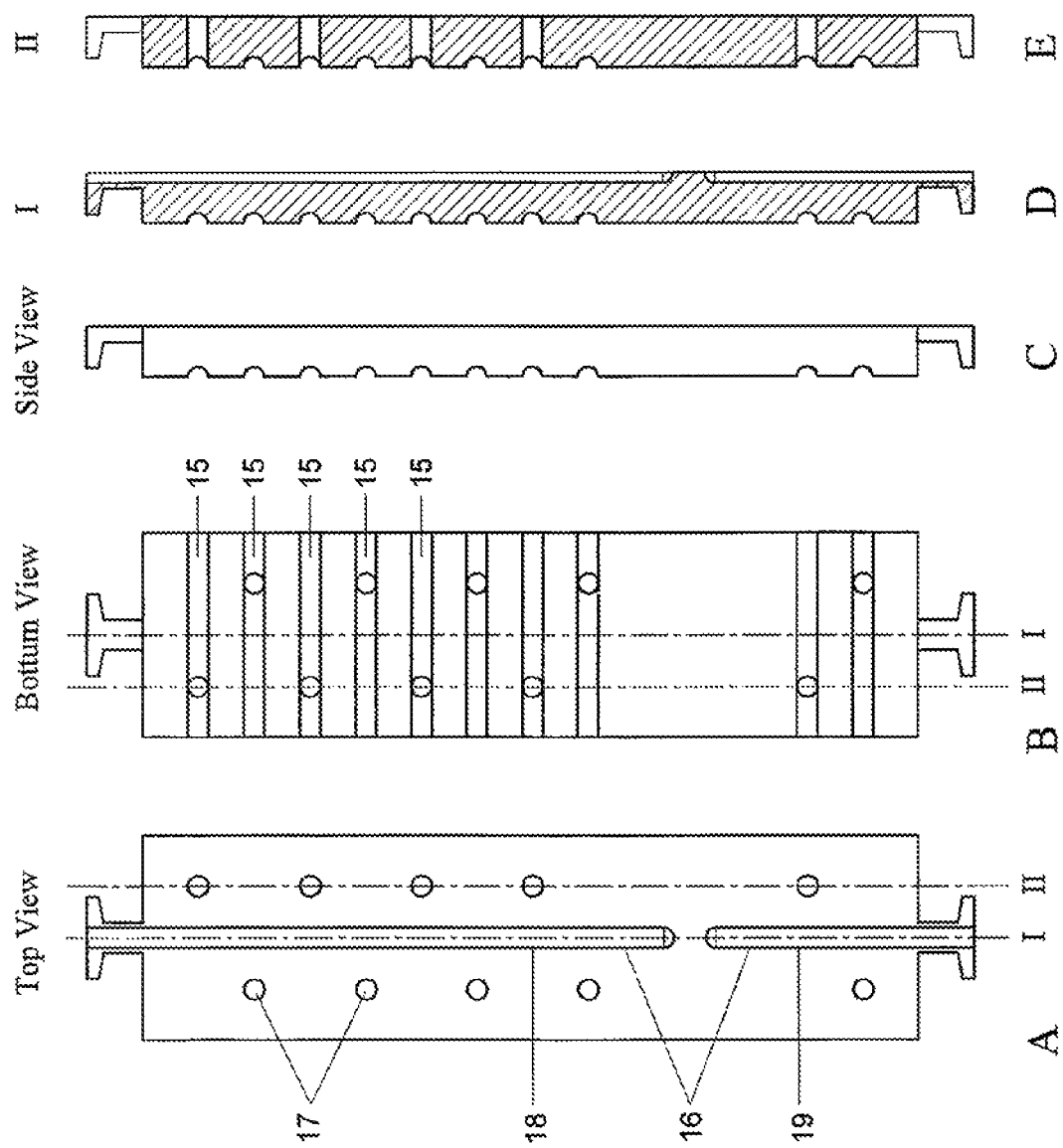
Figure 5:
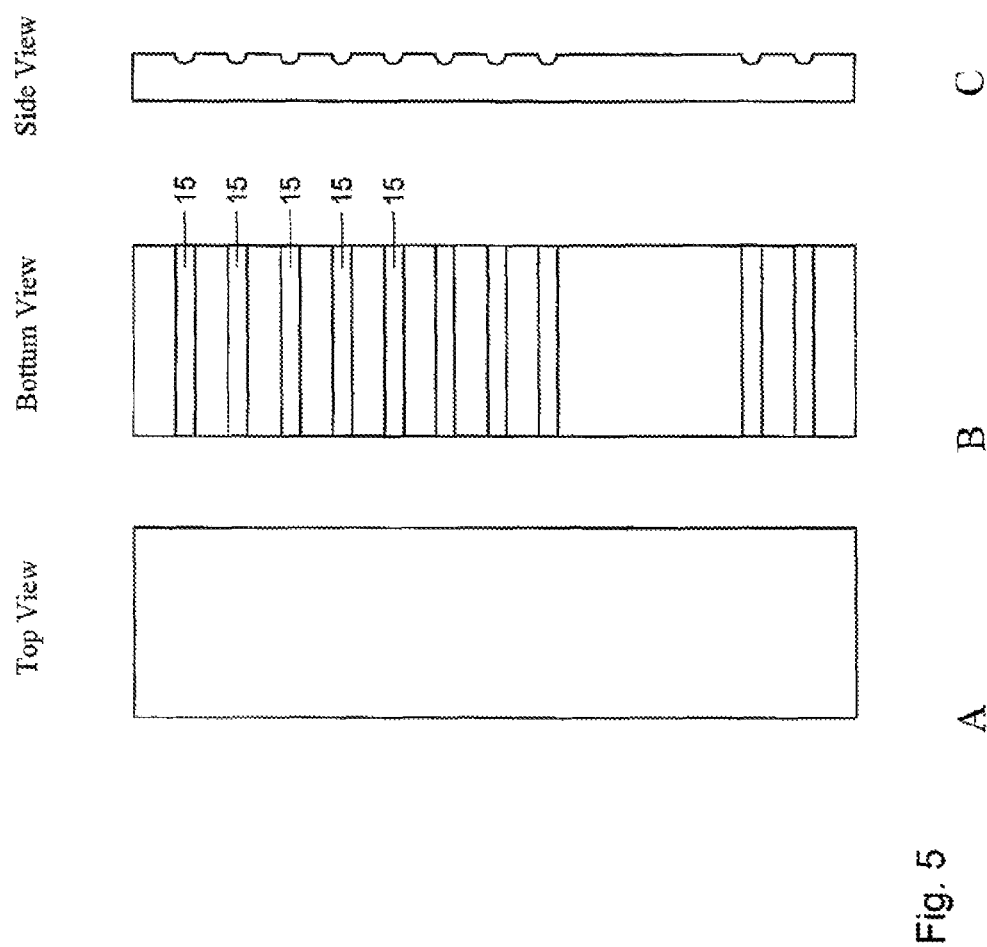

As shown in the subsequent FIG. 3-FIG. 5, the duct layout part 9 comprises a central part 12 (illustrated in FIG. 4) coupled between a base part 13 (FIG. 5) and a cover part 14 (FIG. 3); one side of the central part 12 corresponding a branch duct structure 15; and an opposite side of the central part 12 corresponding to a central duct structure 16, the central part 12 comprising through holes 17 to correspond with through holes 17 provided in a cover part 14; the cover part 14 being coupled to the membrane part 10 for closing a through hole 17 so as to form a membrane valve 8 between the central duct structure 16 and the branch duct structure 15. In the figures, for reasons of clarity, only a limited number of items is identified and corresponding items are not individually referenced.

Specifically, FIGS. 3 and 4 show, from left to right, a top view (A), a bottom view (B), a side view (C) and cross sectional views D and E through sections I-I and II-II respectively indicated in the top and bottom views A and B. FIG. 5 shows from left to right a top view (A), a bottom view (B) and side view (C).

It can be seen in FIG. 3 and FIG. 4 that the central duct structure 16 is formed by ducts 18 and 19 that are connected, via the trough holes 17, and the central duct valve 6.

In addition, the cover part 14 may also contain the diaphragm 10 of these valves. Alternative, the diaphragm 10 can be provided by a separate construction part. The diaphragm 10 comprises a flexible membrane 20 (see FIG. 6) that can close or open the connections between the system in- or outlets and the column in- or outlets in this part of the manifold 1.

In the said example, the cover part 14 may be arranged to carry actuators 11 that can press or release the membranes against said duct layout part 9, thereby opening or closing a membrane valve 8. These actuators 11 can be of any kind. Commonly used actuators operate on electromagnetic force or pneumatic pressure.

FIG. 6 shows in more detail the construction of a valve membrane 6 and/or 8 according to the invention. In FIG. 6A, the valve is shown in an open position, in FIG. 6B, the valve is shown in a closed position. Here, the cover part 14 is shown to have through holes which are in fluid communication with the branch ducts (not shown) and central duct (not shown).

The through holes 17 are formed in a pocket 21 which is covered by a flexible membrane 20. By pressing the membrane 20 in the pocket 21, the flow through the through hole is stopped and the valve 8 is closed.

In case said first part does not already include a diaphragm that can close or open the connections between the system in- or outlets and the column in- or outlets in this part of the manifold 1, the manifold 1 may comprise a third part which comprises or which carries the diaphragm 20.

Once assembled together, the two or three parts (base part 13, central part 12, cover part 14) combine to one manifold 1 with multiple diaphragm valves 8. The diaphragm valves 8 each may have their own actuator 11 and may each be individually controlled.

The only wetted parts in the valve manifolds are the duct layout part 9 and—if applicable—the membrane part 10, being the membrane 20 of the diaphragm valves 8. These parts of the valve manifold are preferably designed for single-use or dedicated-use.

Figure 7:
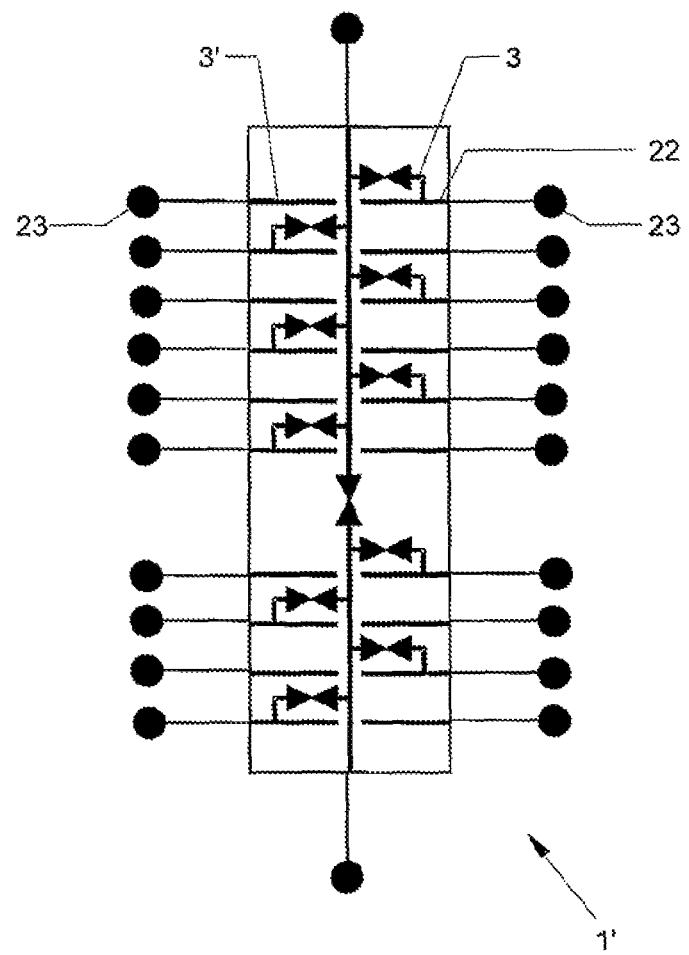
FIG. 7 schematically depicts the system inlets and system outlets of each manifold F.

In one aspect of the invention, the system inlets and system outlets of each manifold 1' actually pass through the manifold as is schematically depicted in FIG. 7. That is, preferably, at least one branch duct 3 comprises another branch 22 to form a branch duct 3' between at least two branch connectors 23, the branch duct 3' in fluid communication and closable from the central duct 2. This allows connecting manifolds to each other without a separate distributor. Each of the system in- and outlets is connected to one end of a series of manifolds, while the other end of the series can be closed by a valve or may be permanently closed. This connection between two subsequent manifolds can be done by sanitary couplings between the different in- and outlets, for instance through tri-clover connections. In that case, every system in- and outlet requires one clamp between two adjacent manifolds.

Figure 8:
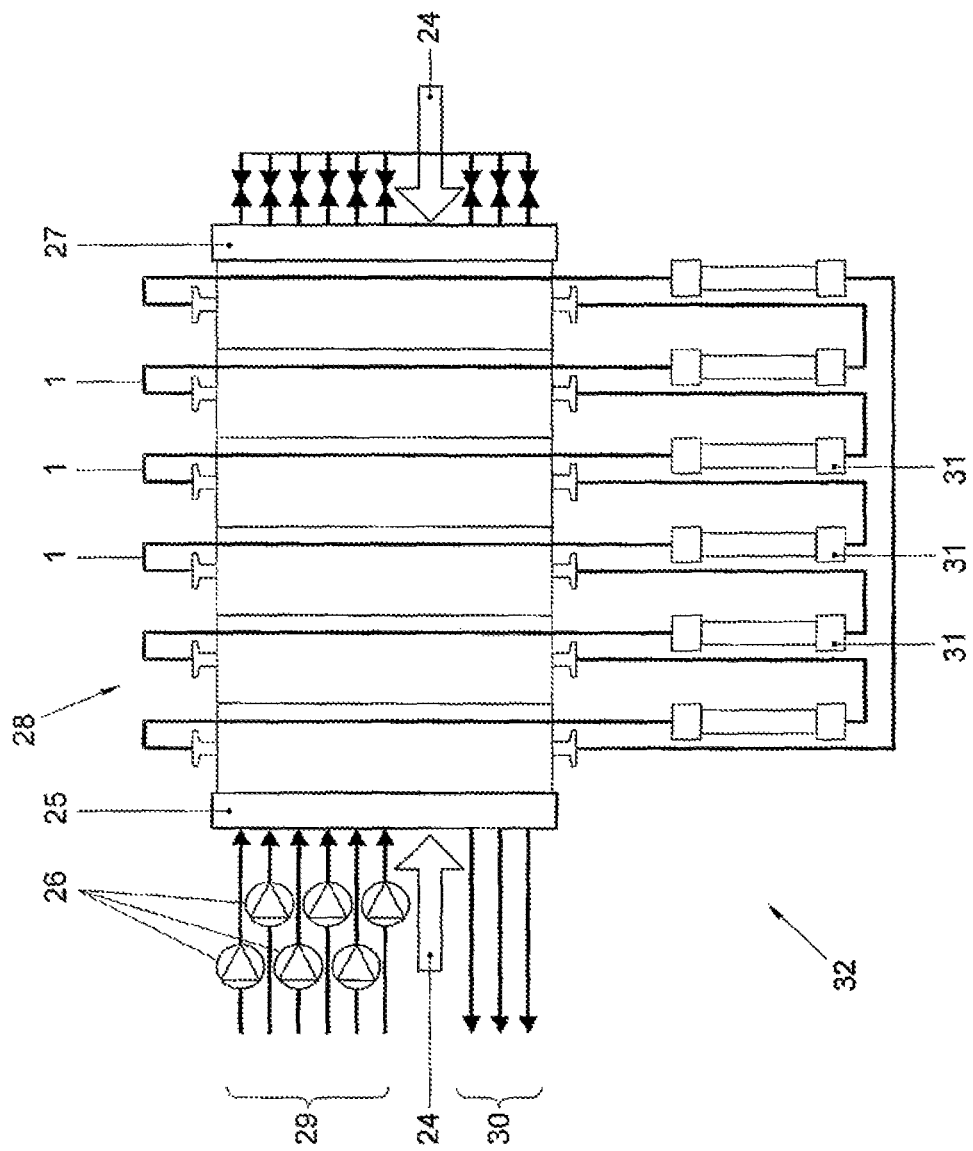
FIG. 8 shows the connectors of a gasket type.

Alternatively, a pocket for the gasket can be molded in the side surfaces of the manifold in such a way that these gaskets ensure leak-tight connections between the adjacent manifolds. In this case, the manifolds should be tightly pressed together by some means such as a press 24 or the like as is schematically depicted in FIG. 8. Yet another alternative is that the gaskets of all connections are combined in one layer that should be put in between two adjacent manifolds. In such a case, the manifolds may be equipped with a fitting to ensure proper positioning of the gasket. In this case, the sealing is again ensured by pressing the manifolds tightly together. This can, for instance be done, by enclosing the manifolds between a front member 25 that connects all system in- and outlets towards pumps 26, vessels, containers, etc., and a rear member 27 that may contain (manual) valves or that may even close all in- and outlets from the last manifold. Said front and rear members 25, 27 are firmly pressed together, thereby pressing all manifolds together and ensuring proper sealing of the connections between these manifolds. FIG. 8 shows an exemplary embodiment of a multiple of manifolds 1 pressed together to form a single valve unit 28 comprising of modular pieces 1. The valve unit 28 is coupled between system inlets 29 and outlets 30 and columns 31 coupled to form a chromatographic separation system 32.

In one aspect of the invention, the system consists of three columns with valve manifolds in between them. Each of these manifolds has minimal three inlets and minimal two outlets. This combination allows continuous a process as normally conducted in a merry-go-round system. This involves continuous feeding of at least one column, generally two columns in series. The third column is washed, eluted and/or regenerated while the first and second column are being loaded. After a certain time, once the first column is saturated, the valves in the manifolds switch in such a manner that the feed solution is applied on the second column, while said first column is subjected to all other steps in the process. The third column is connected to the outlet of the second column.

In one aspect of the invention, the system comprises four to eight columns with valve manifolds in between them. Each of these manifolds comprises at least three inlets and at least three outlets. This combination allows continuous fractionation processes, similar to the traditional SMB processes. Since the valves are controlled individually, the length of the different zones in the SMB process does not necessarily have to be constant during the operation and not all flow rates are necessarily constant over the entire process cycle. The system according to this aspect of the invention thus also allows more advanced operations than traditional SMB chromatography, such as the Improved SMB, Sequential SMB, Varicol or the Japan Organo mode of operation.

In one aspect of the invention, the system comprises eight or more columns with valve manifolds in between them. Each manifold has minimal five, preferably eight inlets and minimal two, preferably four outlets. This combination allows continuous countercurrent purification of complex proteins, such as monoclonal antibodies, using ion exchange or affinity chromatography. Each of the different fluids involved is connected to one inlet of the system. The valves on the manifolds are controlled in such a way that the columns are subsequently subjected to the loading, washing, elution and all other steps involved in the process cycle. Since multiple columns can be connected in series one or more of these steps can be carried out in essentially countercurrent mode. This enables a more efficient process and may lead to significant savings in chemicals, solvents and water.

In one aspect of the invention, the system comprises a single column and a single valve manifold. A pump is connected to the column inlet of the valve manifold and transfers the fluids from the valve manifold to the column inlet. The column outlet is connected to the column outlet of the valve manifold. The system inlets and system outlets are connected to respectively product or waste collection tanks. This system allows conducting traditional single column chromatographic purifications with one disposable valve manifold. The valves are controlled such that all process solutions are pumped into the column in the appropriate order. The valve that connects the column inlet and column outlet in the valve manifold remains closed at all time.

In one aspect of the invention, the system comprises multiple columns, each carrying a different Adsorbent. This allows conducting fully automated multi-step chromatographic purifications. This may or may not involve intermediate storage connected to the system outlets, which is also connected to a system inlet.

EXAMPLES

Figure 9:
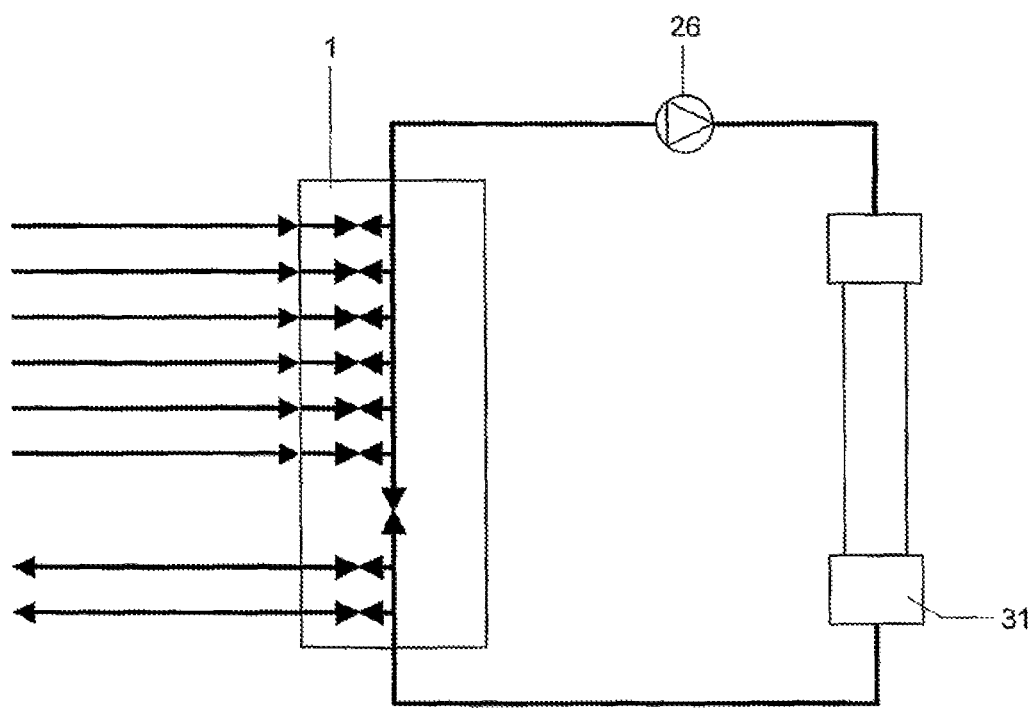
FIG. 9 shows a single column set-up for performing traditional chromatographic separations.

With reference to FIG. 9 a single column set-up is shown for performing traditional chromatographic separations. The assembly consists of one column 31, one manifold 1 and one pump 26. The pump 26 is used to transfer fluids from the valve manifold 1 towards the column 31. The valve manifold is used to select the appropriate solution from the storage containers (not drawn) and to direct the column effluent to either waste or product collection container (not drawn). During normal operation, the central valve 6 of the valve manifold 1 is closed. It is obvious that this scheme can involve as many inlets and outlets as required for the separation.

Figure 10:
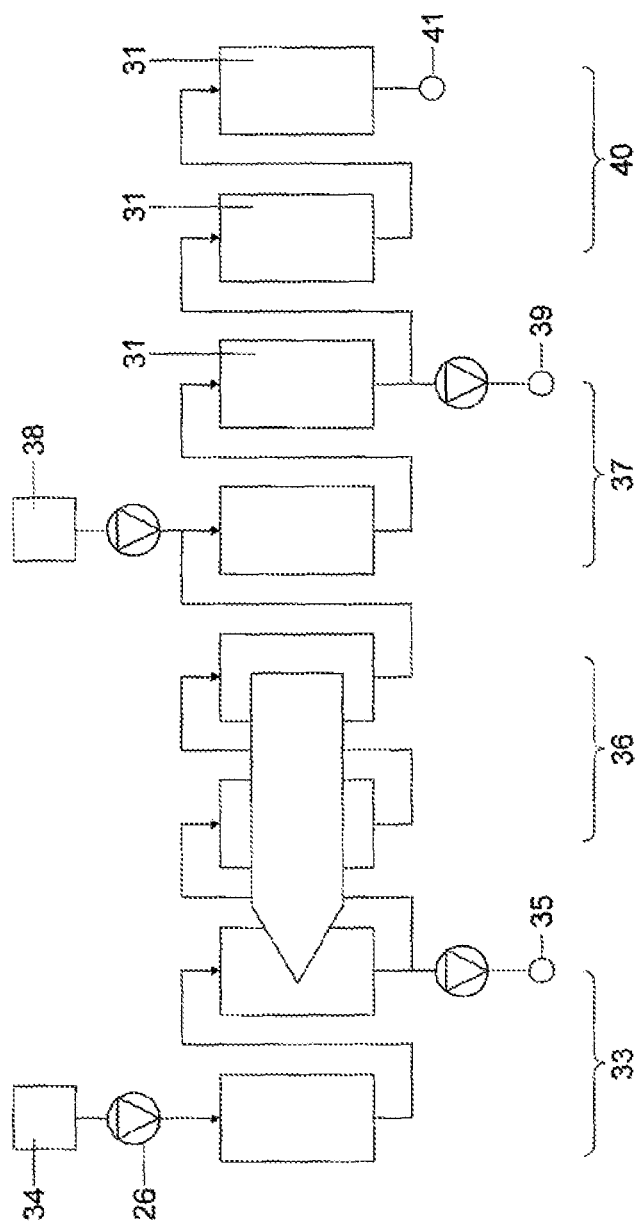
FIGS. 10 and 11 illustrate a complex scheme for fractionating SMB set-up (2-2-2-2 configuration).
Figure 11:
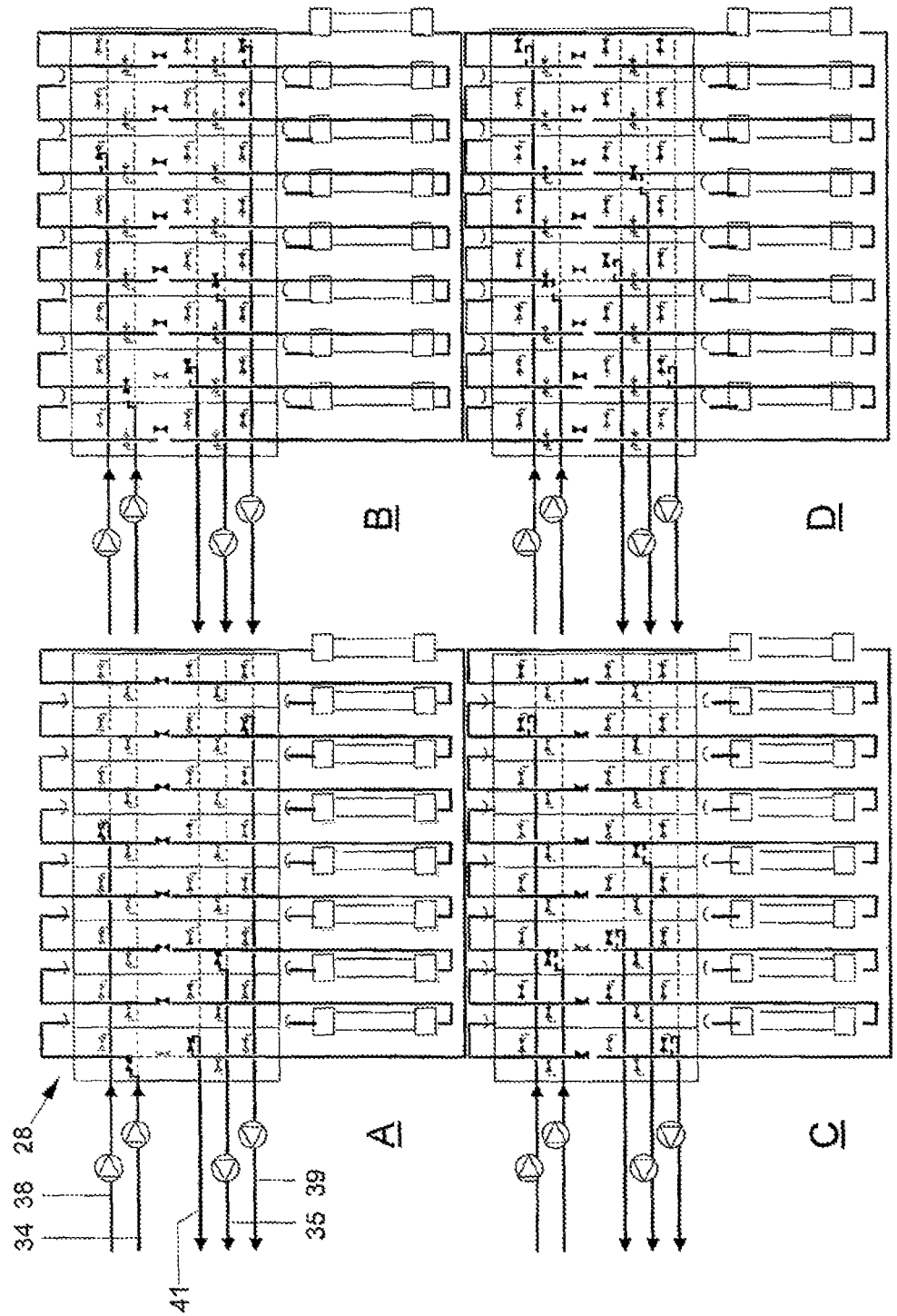

With reference to FIG. 10 and FIG. 11 a more complex scheme is illustrated for fractionating SMB set-up (2-2-2-2 configuration). The assembly comprises eight serially connected columns 31, four pumps 26 and eight manifolds 1. In this scheme, a first zone 33 is formed by two serially coupled columns 31 connected to a storage tank 34 containing a desorbent; and connected to an outlet for providing an Extract product stream 35. The second zone 36 also comprises a pair of serially coupled columns 31 connected to the first zone 33. The second zone 36 is fed by a part of the effluent of the first zone. A third zone 37 is fed by the effluent of the second zone 36 and by a flow from a feed solution container 38. The third zone 37 is connected to an outlet providing the Raffinate product stream 39. The fourth zone 40 is serially connected to the third zone and provides a clean desorbent 41 which can be recycled.

As shown in FIG. 11 the valve manifolds are organized in such a way that all branch ducts for system flows are connected to each other. This can be done by a distributor (not shown) or, preferably, by using valve manifolds that can be interconnected (as shown in FIG. 7). The latter option is shown in FIG. 8. The outlets of the last valve manifold are closed (not shown).

In a method for providing biopharmaceutical products involving a chromatographic separation process, the system can be used as shown in FIG. 11. In this FIG. 11, in particular the first four steps of valve switching arrangements are depicted, effectively providing a simulated moving bed by alternatingly switching subsequent columns 31. In particular, in A, the first column is fed by Desorbent flow 34, whereas the fifth column is fed by Feed solution 38. The recycle, extract and raffinate streams are provided by the second, the sixth and the eight column by appropriate switching arrangements in the coupled modular valve manifolds 1 according to the invention. In subsequent steps, the switching configuration is adapted as can be shown in sub figures B-D, wherein for each column, a subsequent column is switched, effectively providing a simulating moving bed arrangement.

Figure 12:
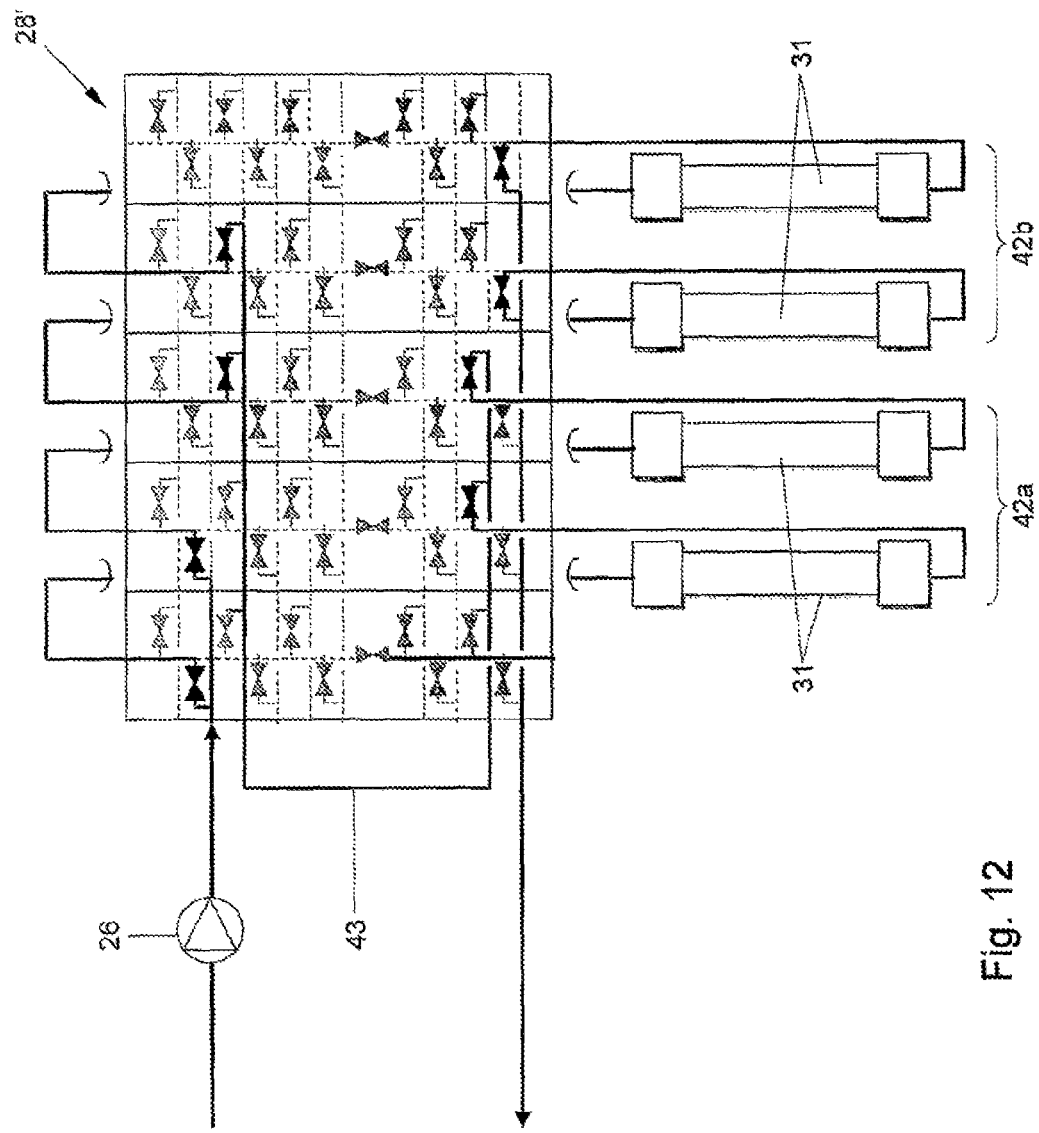
FIG. 12 shows two serially switched sets 42a42b, each set including two parallel columns 31.

Furthermore, FIG. 12 shows two serially switched sets 42a 42b, each set comprising two parallel columns 31. The switching arrangement 28' thus provides a pair of parallel coupled columns 31 using the modular valve manifolds 1 according to the invention. In particular, an external loop 43 effectively provides a parallel coupling of the columns 31.

Figure 13:
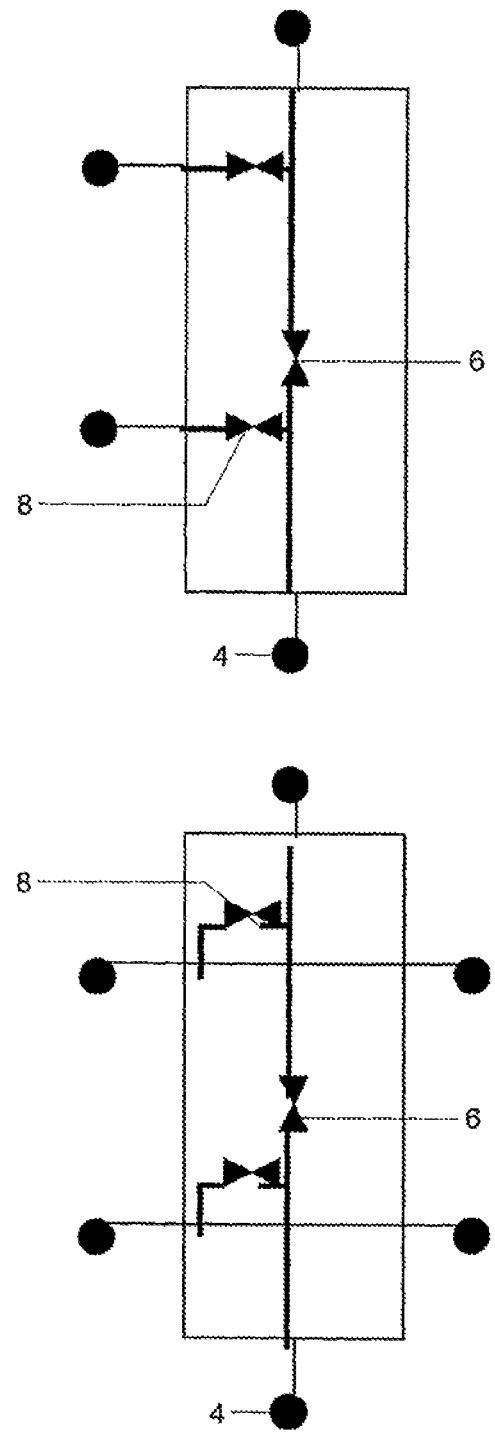
FIG. 13 shows valve manifold arrangements which can be coupled either parallel or serially to provide a manifold having a plurality of connectors.

FIG. 13 shows a number of valve manifold arrangements that are deemed to fall within the scope of the invention and which can be coupled either parallel or serially to provide a manifold comprising a plurality of connectors; at least one central duct between at least two opposite connectors forming an inlet and an outlet respectively, the duct comprising a closable duct valve; and at least one branch duct branching from the central duct to a branch connector, the branch duct comprising a closable branch valve. The valve arrangement can be coupled to provide more complex valve manifolds wherein plural feeds and drains are provided for feeding and draining the central duct.

Although the invention has been described with reference to the exemplary embodiments, the invention is not limited thereto. For instance, the device can be made of a single constituent piece or several pieces with specific duct structures, which can include all kind of additional branching and valving structures. The invention is not limited to the membrane valves of the type disclosed but could incorporate other kinds of valves with adequate functional characteristics. These and other modifications are deemed to fall within the scope of the invention, as claimed in the annexed claims.

The invention claimed is:

1. A continuous purification method for chromatographic separations comprising:
    connecting a plurality of connectors of a manifold to one or more chromatographic separation columns and/or feed or extraction tubing;
    providing at least one central duct between at least two connectors forming an inlet and an outlet to the manifold respectively, the duct comprising a closable duct valve;
    providing a plurality of branch ducts branching from the central duct to a branch connector; and
    positioning at least one branch duct between the inlet and the central duct valve and at least one branch duct between the outlet and the central duct valve; further comprising continuously pumping feed and or extraction flow through said columns and tubes; wherein, during chromatographic separation, at least two process steps of a loading, washing, eluting, regenerating and equilibrating are simultaneously carried out in respective process zones formed by columns that may be connected by an open central duct valve in open position; which process zones are separated by a central duct valve in closed position.

2. A method according to claim 1, wherein, in the chromatographic separation a biopharmaceutical product is yielded in an extraction tube.

3. A method according to claim 1, wherein a system outlet is provided for intermediate storage.

4. A method according to claim 1, comprising a single column arrangement, wherein, during the separation process, the central duct remains closed.

5. A method according to claim 1 wherein said process zones are formed by a first zone of serially coupled columns connected to a storage tank of desorbent; a second zone of serially coupled columns fed by an effluent of the first zone; a third zone fed by the effluent of the second zone and by a flow from a feed solution container; and connected to an outlet providing a raffinate product stream; and connected to a fourth zone serially connected to the third zone and providing a clean desorbent; and wherein each subsequent column is switched so as to provide a simulating moving bed arrangement.

* * * * *

UNITED STATES PATENT AND TRADEMARK OFFICE
CERTIFICATE OF CORRECTION

PATENT NO. : 8,828,234 B2  
APPLICATION NO. : 12/962488  
DATED : September 9, 2014  
INVENTOR(S) : Marc Antonius Theodorus Bisschops et al.

Page 1 of 1

It is certified that error appears in the above-identified patent and that said Letters Patent is hereby corrected as shown below:

Title page item (75), line 1, first inventor "Marc Abtonius Theodorus Bisschops" should read -- Marc Antonius Theodorus Bisschops --

Signed and Sealed this  
Ninth Day of December, 2014

Michelle K. Lee  
*Deputy Director of the United States Patent and Trademark Office*